United States Patent [19]

Burke et al.

[11] Patent Number: 5,281,210
[45] Date of Patent: Jan. 25, 1994

[54] ACCUMULATOR FOR IMPLANTABLE PUMP

[75] Inventors: Paul F. Burke, Woonsocket, R.I.; Samir F. Idriss, Hyde Park, Mass.

[73] Assignee: Infusaid, Inc., Norwood, Mass.

[21] Appl. No.: 946,848

[22] Filed: Sep. 18, 1992

[51] Int. Cl.⁵ .......................................... A61M 31/00
[52] U.S. Cl. ................................. 604/891.1; 604/141
[58] Field of Search .............. 604/891.1, 141, 140, 604/153; 128/DIG. 12

[56] References Cited

U.S. PATENT DOCUMENTS

| | | | |
|---|---|---|---|
| 4,299,220 | 11/1981 | Dorman | 604/141 |
| 4,668,231 | 5/1987 | de Vries et al. | 604/891.1 |
| 4,699,615 | 10/1987 | Fischell et al. | 604/153 |
| 4,820,273 | 4/1989 | Reinicke | 604/891.1 |
| 4,838,887 | 6/1989 | Idriss | 604/891.1 |
| 4,969,873 | 11/1990 | Steinbach et al. | 604/891.1 |
| 5,049,141 | 9/1991 | Olive | 604/891.1 |
| 5,053,031 | 10/1991 | Borsanyl | 604/891.1 |
| 5,090,963 | 2/1992 | Gross et al. | 604/141 |
| 5,137,529 | 8/1992 | Watson et al. | 604/891.1 |

Primary Examiner—Paul J. Hirsch
Attorney, Agent, or Firm—Sughrue, Mion, Zinn, Macpeak & Seas

[57] ABSTRACT

An accumulator for an implantable infusion system employs a pair of separated diaphragms movable in unison by a transfer fluid disposed therebetween. A first chamber receives infusate in metered amounts and dispenses the contents as a function of toggled valve operation. During filling, the first diaphragm deflects upward and by pressure transfer causes a corresponding deflection in the second diaphragm. The second diaphragm is biased by springs, gas under pressure or the like. Hence, when the outlet valve opens, the pressure differential across the diaphragm causes downward deflection. No mechanical stops are needed in the infusate chamber for the first diaphragm since its movement is controlled by the pressure differential across the second diaphragm.

25 Claims, 2 Drawing Sheets

ACCUMULATOR FOR IMPLANTABLE PUMP

BACKGROUND OF THE INVENTION

This invention relates to an implantable infusion system. In particular, it relates to an improvement in an infusate accumulator used with a valve system in such a system operating at positive pressure to dispense medication in accordance with different specified flow rates.

Implantable infusion pumps utilizing an accumulator positioned between a pair of valves which alternately open and close are disclosed in U.S. Pat. Nos. 4,838,887 and 5,049,141, commonly assigned. The disclosure of the '887 patent is expressly incorporated herein by reference. In such a system, as illustrated in FIG. 1, a drug reservoir 10 is refillable by means of a septum 12. The reservoir comprises a sealed housing 14 containing a bellows element 16 having a chamber 18 which comprises the drug reservoir. The bellows 16 separates the housing 14 into a second zone 20 which is normally filled with a two-phase fluid. The fluid, normally Freon, vaporizes and compresses the bellows 16 thus providing a release pressure to the reservoir 18 through the outlet leading to the infusion site. During the refill process chamber 18 is loaded with medication via the septum 12. The two-phase fluid is then pressurized condensing a portion of the vapor and returning it to the liquid phase.

Such systems also employ an outlet filter 24 and a side port 27 for direct bolus injections. The reservoir and fluid delivery techniques are well established in constant flow systems. To provide for increased accuracy in delivery dosage, the use of an accumulator 30 has been proposed for use in a number of applications.

These systems employ a metering assembly comprising two normally closed valves 26 and 28. Interposed between the two valves is an accumulator 30. The valves 26 and 28 are controlled electronically by the module 32 which may be programmed utilizing an external programmer 34.

In operation of such a system, a constant positive pressure flow from the reservoir 10 to the inlet valve 26 occurs. Valve 26 is opened while the outlet valve 28 is closed. This loads the accumulator 30 with a predetermined amount of medication. The valve 26 is then closed and outlet valve 28 opened so that the contents of the accumulator 30 are delivered to the catheter 36 for delivery to the infusate site. The rate of switching of the valves 26 and 28 thus determines the frequency of pumping through the system and therefore determines the delivery rate of medication through the catheter 36. For each cycle a constant amount is delivered, the accumulator volume.

In the system illustrated in FIG. 1, the accumulator 30 has two alternative forms as illustrated in FIGS. 2 and 3. For purposes of convenience, FIGS. 2 and 3 utilize the same numbering as in the '887 patent. As illustrated in FIG. 2, the inlet is represented by numeral 58 wherein fluid enters the accumulator from the inlet valve 26. The accumulator comprises a diaphragm 90, a backing plate 92, an end cap 94, and fill tube 96 and a spacer plate 98. The diaphragm 90 deflects in response to fluid entry of the chamber 102. The backing plate 92 acts as a mechanical stop to limit motion of the diaphragm. Similarly, the spacer plate 98 is used to limit diaphragm motion during discharge, that is, the passage of fluid through the outlet 59.

The use of the spacer plate 98 as a mechanical stop creates a problem when fragile materials such as insulin are used. The material is locally compressed and crushed by the mechanical action of the diaphragm contacting the stop. This breaks down the fluid. Since the internal volumes are quite small, this in turn can result in residue formation inside the accumulator.

The fill tube 96 is used to supply an inert gas to the chamber 104. The purpose of chamber 104 is to provide a region which is charged at a pressure lower than that of the infusate pressure in drug reservoir 18 so that accumulator chamber 102 fills when inlet valve 26 is opened, but higher in pressure than that of the catheter 36 to allow the diaphragm 90 to deflect back to the spacer plate 98 position as the chamber 102 empties when the outlet valve 28 is opened. Additional details of this accumulator may be found in U.S. Pat. No. 4,838,887.

FIG. 3 illustrates an alternative configuration. In this alternative arrangement, the backing plate 92 comprises three elements which electrically isolate the center of the plate from the diaphragm 90. A supply of inert gas is still supplied via the feed fill tube 96. A lead 110 is attached to a flange forming a portion of the end cap assembly. A ceramic cup 113, which is lined with metal 111, provides a conductive path between a stop 114 and the lead 110. The diaphragm 90 is used as a moving switch contact. This provides a signal indicating that the accumulator is full, that is, the diaphragm in an upward position contacting the stop 114. This electrical signal is used for diagnostic determinations of the system such as leaks in the valve. Again, more complete details as to the use of the modified accumulator of FIG. 3 are found in the '887 patent.

A problem with these types of accumulators is the formation of precipitate on the spacer plate. Over time this build-up deteriorates the flow accuracy in the system and in an extreme case causes blockage. U.S. Pat. No. 5,049,141 addresses this problem by minimizing the contact points with the diaphragm. This solution reduces stress points on the fluid within the accumulator. There are however still points of contact and therefore potential damage to the material.

SUMMARY OF INVENTION

The valve accumulator systems discussed herein function in a satisfactory manner and provide for an accurate metering of flow. However, one difficulty common to all valve systems is damage to the fluid passing through it as a consequence of interaction with valves, diaphragms and the like. In particular, various types of insulin are particularly sensitive to mechanically induced damage which tends to break down that material. This in turn causes a build-up of precipitate at the very location in the system, the accumulator, where metering accuracy is desired. Over time clogging can occur.

Therefore, it is an object of this invention to provide an improved accumulator which minimizes damage to sensitive materials passing through an implantable pump system.

Yet another object of this invention is to provide an accumulator configuration having minimal size to thereby reduce the overall packaging of implantable medical devices.

A still further object of this invention is to provide an accumulator which does not utilize mechanical stops or spacer plate contact in the infusate path, thereby minimizing fluid contact points.

These and other objects of this invention are accomplished by means of a dual diaphragm accumulator configuration. The first diaphragm performs the steps of fluid transfer as in prior art systems. The second diaphragm is separated from the first by means of a transfer fluid. The first diaphragm has no mechanical stops associated with it but deflects as a function of the difference in pressure between the drug chamber and the transfer fluid chamber. The second diaphragm deflects between positions and has mechanical stops. It is biased by gas, springs and the like to provide a restoring bias hydraulically to the system, i.e., to cause the first diaphragm to store or expel fluid.

As an alternative to the gas, a spring biased pressure plate may be used or, as an alternative to the transfer fluid, a chamfered slider element may be used.

This invention will be described in greater detail by referring to the drawing and the description of the preferred embodiment which follows.

DESCRIPTION OF THE PREFERRED EMBODIMENT

Figure 1:
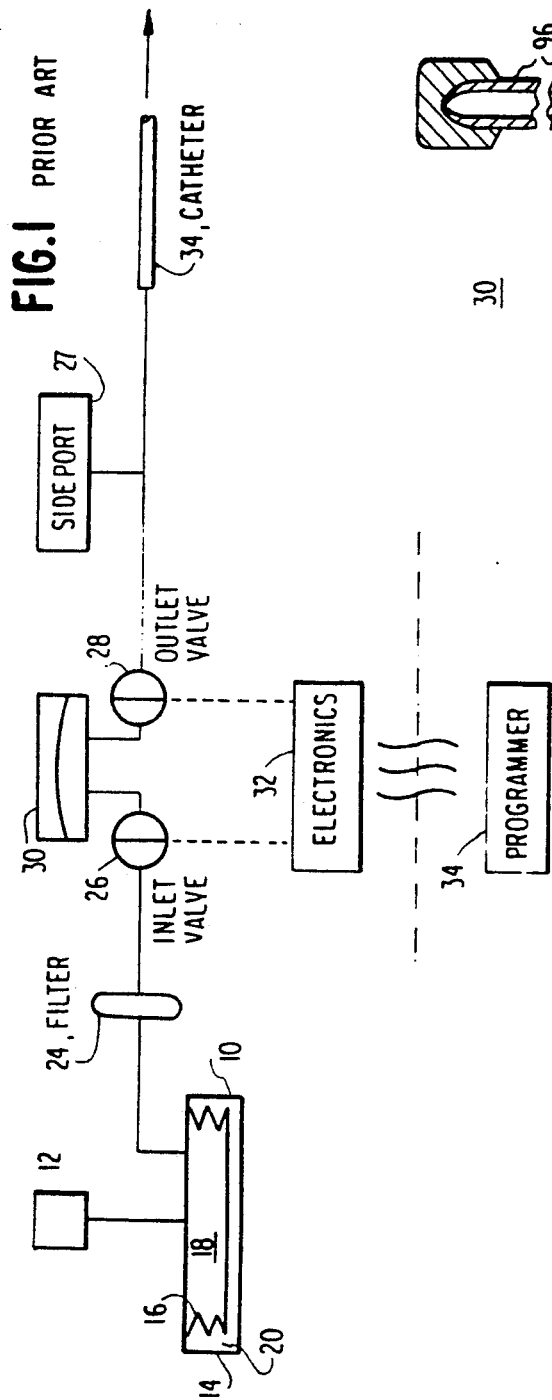
FIG. 1 is a schematic diagram illustrating a complete implantable system which employs an accumulator as described in U.S. Pat. No. 4,838,887.
Figure 3:
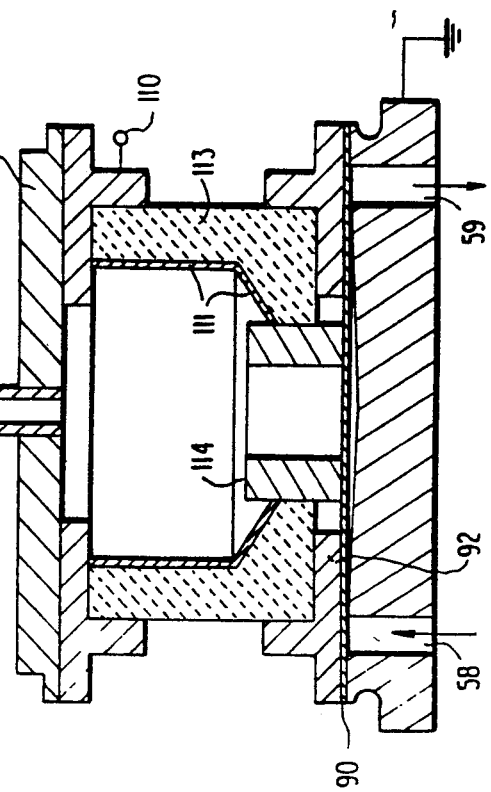
FIG. 3 is a schematic cut-away side view of a modified accumulator illustrated in U.S. Pat. No. 4,838,887.
Figure 4:
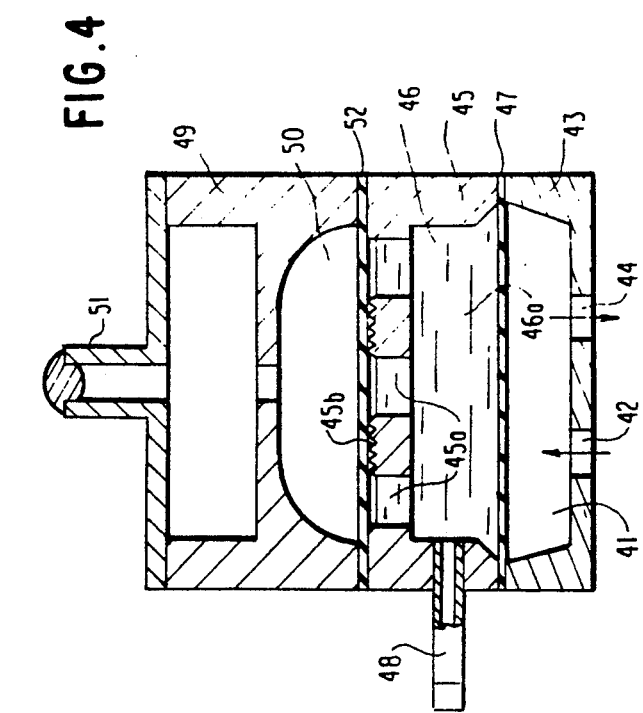
FIG. 4 is a schematic side view of an accumulator in accordance with the first preferred embodiment of this invention.

Referring now to FIG. 4, a first preferred embodiment of this invention is depicted. A drug chamber 41 receives fluid via the inlet 42. It will be understood that the inlet 42 is coupled to an inlet valve, such as element 26 depicted in FIG. 1. The inlet pressure is approximately 8.5 psig. The inlet 42 is formed in the spacer plate 43 which also has an outlet 44 from the drug chamber 41 of the accumulator.

The accumulator of FIG. 4 also includes an intermediate member 45 with flow passages 45a and surface grooves 45b, which defines a transfer fluid chamber 46. The presence of the surface grooves 45b is to allow the fluid to lift the diaphragm quicker thus decreasing the response time to fill from empty. The transfer fluid chamber 46 is separated from the drug chamber 41 by means of a first diaphragm 47. The transfer fluid chamber 46 is filled with transfer fluid 46a via a fill tube 48 which is sealed after the transfer fluid chamber 46 has been loaded.

The transfer fluid 46a may be any incompressible, low vapor pressure fluid such as silicone oil, water, or other material which can be used hydraulically to transfer the pressure difference which exists across first diaphragm 47 through flow passages 45a to a second diaphragm 52. The second diaphragm 52 has a constant back pressure bias based on the pressure in cavity 50. A backing plate 49 defines the cavity 50 which is filled with an inert gas such as Argon loaded to 4 psig, utilizing the fill tube 51 as illustrated. This pressure can urge second diaphragm 52 downward, displacing the transfer fluid 46a in transfer fluid chamber 46 against first diaphragm 47, forcing a reduction in volume of drug chamber 41.

In operation, the first diaphragm 47 displaces as a function of the pressure difference between that which exists in the drug chamber 41 and in the transfer fluid chamber 46. During filling, the input pressure in chamber 41 is greater than the pressure of transfer fluid 46a as biased by the gas in cavity 50. Therefore, the first diaphragm 47 deflects upward which in turn causes second diaphragm 52 to deflect upward. The volume in chamber 46 remains constant since the transfer fluid 46a is incompressible. Similarly, when valve 28 is opened chamber 41 empties as first diaphragm 47 and second diaphragm 52 deflect downward.

Figure 2:
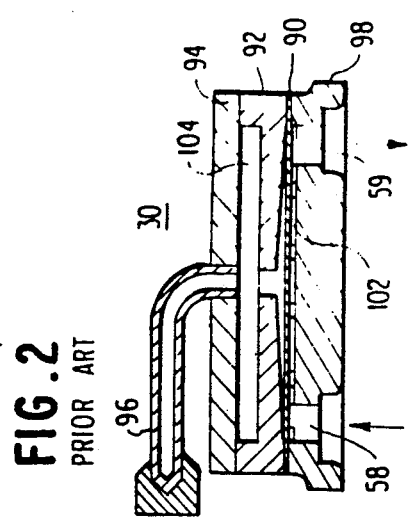
FIG. 2 is a schematic cut-away side view of an accumulator as described in U.S. Pat. No. 4,838,887.

However, the motion of first diaphragm 47 is not controlled by any mechanical stops. Instead, its motion is limited by the volume of transfer fluid 46a displaced in cavity 46 which in turn is limited by the displacement of second diaphragm 52. The position of second diaphragm 52 is maintained by backing plate 49 and intermediate member 45. These elements perform the same function as backing plate 92 and spacer plate 98 in FIG. 2, respectively.

By eliminating mechanical stops, fluid stresses generated in the drug chamber 41 by contact points against accumulator first diaphragm 47 are eliminated. These stresses would tend to produce protein precipitation in the drug chamber 41, hindering accumulator performance. The use of the dual diaphragm accumulator eliminates the need for contact with the spacer plate 98 of FIG. 2 and thus eliminates the problem of damage to the fluid passing therethrough.

It will again be appreciated from the description of this first preferred embodiment that the second diaphragm 52 is in direct fluid communication with the first diaphragm 47 via the transfer fluid 46a in second chamber 46 through flow passages 45a. Consequently, the volume displaced by second diaphragm 52 as it travels between backing plate 49 and intermediate member 45 is the identical volume displaced by first diaphragm 47 as it is urged up and down via the transfer fluid 46a in transfer fluid chamber 46.

Figure 5:
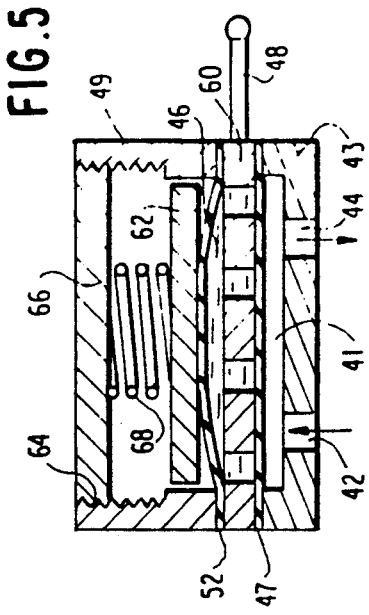
FIG. 5 is a schematic cut-away side view of an accumulator in accordance with a second preferred embodiment of this invention.

FIG. 5 illustrates a second preferred embodiment of this invention. In FIG. 5 like components are designated with the same numerals as in FIG. 4. To the extent that those items function in a similar manner, they will not be discussed with respect to this second preferred embodiment.

FIG. 5 departs from FIG. 4 in several respects. First, a spacer disc 60 having perforations is used in the transfer fluid chamber 46. The perforated disc has a series of holes to allow fluid communication between upper and lower surfaces thereof. The purpose of the disc 60 is to provide mechanical limit stops to both the first and second diaphragms 47 and 52, respectively.

Secondly, FIG. 5 does not utilize a gas back pressure chamber. Rather, a pressure plate 62 provides the necessary bias to second diaphragm 52. Pressure adjustment is accomplished by providing a section of the inner wall of member 49 with a threaded element. A compatible threaded back plate 66 is provided with a spring 68. By threading the plate 66 using threads 64, the spring tension is adjusted thereby providing variable pressure onto the pressure plate 62.

This embodiment therefore eliminates the second pressurized cavity 50. It is apparent however that the perforated disc 60 could be used in conjunction with the embodiment of FIG. 4 while still retaining the back pressure provided by the cavity 50.

The disc 60 has a surface texture characteristic such as micromachined flow channels or is roughened to provide a random flow pattern. Such is desired to decrease the response time of the system in a fashion similar to the use of surface grooves 45b of FIG. 4. That is, the valves need not be held in an open state longer than needed thus reducing battery power requirements.

Figure 6:
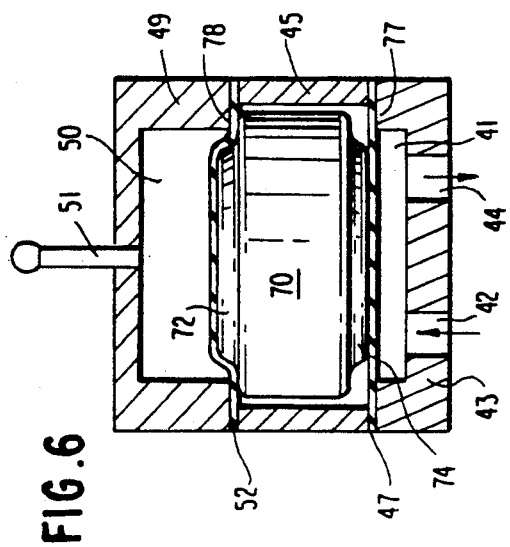
FIG. 6 is a schematic cut-away side view of an accumulator in accordance with a third preferred embodiment of this invention.

Referring now to FIG. 6, a third preferred embodiment of this invention is depicted. In the third embodiment FIG. 6, in place of the perforated disc 60 of the second preferred embodiment, a chamfered slider 70 is used. The slider 70 employs contoured surfaces 72 and 74 on the upper and lower surfaces respectively. As illustrated in FIG. 6, when the slider 70 is biased upward, that is, with the chamber 41 filled, it displaces second diaphragm 52 as illustrated. Conversely, as the chamber 41 empties the slider 70 is lowered given the pressure differential across the second diaphragm 52. The second chamfered surface 74 rests on the lower shoulder 77 of the spacer plate 43. This acts as a limit stop for the slider 70 and thus, first diaphragm 47 will no longer deflect. However, the stop is defined between the side of the first diaphragm 47 and lower shoulder 77 not in fluid contact with the infusate in chamber 41. Thus, that material cannot be damaged during passage through the accumulator. Similarly, an upper shoulder 78 on backing plate 49 acts as a limit stop for the slider 70 to control the upward motion of first diaphragm 47. It should be noted that upper shoulder 78 and/or lower shoulder 77 could also be located on intermediate member 45.

Figure 7:
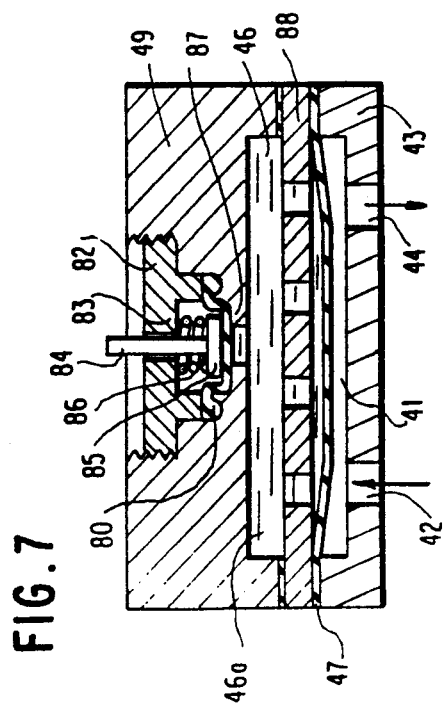
FIG. 7 is a schematic cut-away view of a fourth preferred embodiment of this invention.

A fourth preferred embodiment is illustrated in FIG. 7. In this embodiment, the second diaphragm is in the form of an elastomeric diaphragm 80. The elastomeric diaphragm 80 is clamped in place between the end cap 49 and a pressure spring adjustment member 82 which is threaded into place in a manner similar to that illustrated in FIG. 5. A push pin 84 is spring biased by means of spring 86.

As illustrated in FIG. 7, the position of the pressure spring adjustment member 82 sets the span between a head 85 of the push pin 84 and the upper flange 83 on adjustment member 82. This compresses the spring 86 which varies the back pressure on the pin and thus sets the position of the elastomeric diaphragm 80. The head 85 of the push pin 84 is also limited in motion by the lower flange 87 on backing plate 49.

FIG. 7 illustrates the use of a perforated screen 88. This is an optional element for purposes of safety to limit the upward deflection of the first diaphragm 47. It is however not required.

While not illustrated in FIGS. 6 and 7, it is apparent that the transfer fluid 46a would be loaded into the transfer fluid chamber 46 in a manner identical to that of FIG. 4.

It is apparent from the description of the preferred embodiments herein that other modifications may practiced without departing from the essential scope of this invention. For example, the spacer elements, such as perforated disc 60, can be cantilevered elements and not a perforated disc. Also, a woven element or a porous plug could be substituted for perforated disc 60. Absolute rigidity is required in any case so that the diaphragm is supported.

The slider 70 of FIG. 6 could be modified to include level sensing in the chamber 41 as a function of slider 70 position. This would be done by Hall effect, capacitive pick-up or metallic contact. By placing the sensor in the wall of intermediate member 45, the position of the slider 70 can be determined. The slider 70 would also be given a texture on surfaces contacting the first and second diaphragms 47 and 52, respectively, to increase flow-thru characteristics thus reducing power requirements.

Having described our invention, we claim:

1. An implantable infusion apparatus comprising:
   a rechargeable positive pressure infusate reservoir;
   metering means receiving infusate from said reservoir and outputting a series of volume spikes, said metering means comprising first and second valves and an accumulator in fluid communication with each of said valves, said first valve positioned between said infusate reservoir and said accumulator and said second valve positioned between said accumulator and an outlet; and
   said accumulator comprising a housing having an infusate chamber, a first diaphragm, a second chamber containing a transfer fluid and separated from said first chamber by said first diaphragm, a second diaphragm in contact with said transfer medium and, means to bias said second diaphragm for deflection toward said first diaphragm.

2. An implantable infusion apparatus of claim 1, wherein said means to bias said second diaphragm comprises a sealed gas chamber charged with a fluid under pressure.

3. The implantable infusion apparatus of claim 1 further comprising contact means apart from said infusate chamber to limit deflection of at least two surfaces of said first and second diaphragms.

4. An implantable infusion apparatus of claim 3, wherein said contact means comprises a movable member in said second chamber.

5. An implantable infusion apparatus of claim 3, wherein said contact means comprises a rigid member in said second chamber.

6. An implantable infusion apparatus of claim 1, wherein said means to bias said second diaphragm comprises a pressure plate in contact with said second diaphragm and spring means to apply a bias force to said pressure plate.

7. An implantable infusion apparatus of claim 6, wherein said spring means comprises a member threaded in said housing, a spring coupled to said pressure plate and to said threaded member whereby said spring is compressed as said threaded member is threaded into said housing.

8. An implantable infusion apparatus of claim 7, wherein said pressure plate comprises a pin having an end plate attached thereto, said spring placed around said pin and means to determine the position of said pin.

9. An implantable infusion apparatus of claim 3, wherein said contact means comprises a perforated member in said second chamber.

10. An implantable infusion apparatus of claim 1, wherein said transfer medium is an incompressible fluid and said accumulator further comprises means to fill said second chamber with said incompressible fluid.

11. An implantable infusion apparatus of claim 4 with said movable member having sides contacting internal shoulders in said housing to limit movement thereof.

12. An implantable infusion apparatus of claim 1, wherein said transfer medium comprises a moveable member in said second chamber.

13. An accumulator for an implantable infusion apparatus comprising:
a housing having an infusate chamber, a first diaphragm, a second chamber containing a transfer medium and separated from said first chamber by said first diaphragm, a second diaphragm in contact with said transfer medium, means to bias said second diaphragm for deflection toward said first diaphragm and, contact means apart from said infusate chamber to limit deflection of at least two surfaces of said first and second diaphragms.

14. An accumulator of claim 13, wherein said means to bias said second diaphragm comprises a sealed gas chamber charged with a fluid under pressure.

15. An accumulator of claim 13, wherein said contact means comprises a movable member in said second chamber.

16. An accumulator of claim 13, wherein said contact means comprises a rigid member in said second chamber.

17. An accumulator of claim 13, wherein said means to bias said second diaphragm comprises a pressure plate in contact with said second diaphragm and spring means to apply a bias force to said pressure plate.

18. An accumulator of claim 17, wherein said spring means comprises a member threaded in said housing, a spring coupled to said pressure plate and to said threaded member whereby said spring is compressed as said threaded member is threaded into said housing.

19. An accumulator of claim 18, wherein said pressure plate comprises a pin having an end plate attached thereto, said spring placed around said pin and means to determine the position of said pin.

20. An accumulator of claim 19, wherein said contact means comprises a perforated member in said second chamber.

21. An accumulator of claim 13, wherein said transfer medium is an incompressible fluid and said accumulator further comprises means to fill said second chamber with said incompressible fluid.

22. An accumulator of claim 15, wherein said movable member has sides contacting internal shoulders in said housing to limit movement thereof.

23. An accumulator of claim 22 further comprising means to determine the position of said movable member.

24. An accumulator of claim 13, wherein said contact means has surface characteristics on major surfaces thereof to promote flow between said major surfaces and said diaphragm surfaces.

25. An accumulator of claim 13, wherein said transfer medium comprises a moveable member in said second chamber.

* * * * *